United States Patent
Che et al.

(10) Patent No.: US 7,378,527 B2
(45) Date of Patent: May 27, 2008

(54) PROCESS FOR THE PREPARATION OF TORSEMIDE AND RELATED INTERMEDIATES

(76) Inventors: Daqing Che, 31 Thornton Drive, Brantford, Ontario (CA) N3R 7L6; Bhaskar Reddy Guntoori, 26 Sudds Lane, Brantford, Ontario (CA) N3T 6M5; Sammy Chris Duncan, 411-65 Sympatica Crescent, Brantford, Ontario (CA) N3P 1M7

( * ) Notice: Subject to any disclaimer, the term of this patent is extended or adjusted under 35 U.S.C. 154(b) by 232 days.

(21) Appl. No.: 10/800,740

(22) Filed: Mar. 16, 2004

(65) Prior Publication Data

US 2005/0209460 A1     Sep. 22, 2005

(51) Int. Cl.
*C07D 211/72*     (2006.01)
(52) U.S. Cl. ..................................... 546/309
(58) Field of Classification Search ............... 546/309
See application file for complete search history.

(56) References Cited

U.S. PATENT DOCUMENTS

| | | | |
|---|---|---|---|
| 3,904,636 A | * | 9/1975 | Delarge et al. ............ 546/291 |
| 4,018,929 A | * | 4/1977 | Delarge et al. ............ 514/335 |
| 4,244,950 A | | 1/1981 | De Ridder et al. ...... 424/248.5 |
| RE30,633 E | | 6/1981 | Delarge et al. ............ 424/263 |
| 6,635,765 B2 | | 10/2003 | Kordova .................... 546/293 |
| 6,670,478 B2 | | 12/2003 | Kordova .................... 546/293 |

FOREIGN PATENT DOCUMENTS

| WO | WO 01/70226 | * | 9/2001 |
| WO | 03097603 | * | 11/2003 |
| WO | WO 03/097603 | | 11/2003 |

OTHER PUBLICATIONS

Wouters et al , Eur. J. Med. Chem. vol. 35 pp. 923-929 (2000), "Isosteriam among analogues of torasemide".*

* cited by examiner

*Primary Examiner*—Janet L. Andres
*Assistant Examiner*—Raymond Covington

(57) ABSTRACT

A process for preparing torsemide or salts thereof comprising:
a) reacting II with isopropyl isocyanate in the presence of an alkali carbonate or bicarbonate and an organic solvent to form an alkali torsemide mixture,
b) recovering the alkali torsemide mixture, and
c) if desired, recovering the torsemide by acidification of the alkali torsemide mixture.

10 Claims, No Drawings

PROCESS FOR THE PREPARATION OF TORSEMIDE AND RELATED INTERMEDIATES

FIELD OF INVENTION

The present invention relates to an improved process for making torsemide and intermediates useful in the preparation of torsemide.

BACKGROUND OF THE INVENTION

Torsemide, chemically named N-[[(1-methylethyl)amino] carbonyl]-4-[(3-methylphenyl) amino]-3-pyridinesulfonamide III, is a loop diuretic which has been found to be particularly effective for the treatment of edema associated with chronic renal failure.

The synthesis of torsemide is described in prior art documents including: Delarge et al, *Ann. Phann. Fr.*31, 467-474 (1973); Delarge et al, *Mem. Acad. R. Med. Belg.* 47(3), 131-210 (1974); DE 2,516,025 ; U.S. Pat. No. 4,244, 950; U.S. RE 30,633; and WO 03/097603 all of which are incorporated herein by reference.

A common process for the preparation of the torsemide III from 4-chloro-3-pyridinesulfonamide I, via intermediate 4-[(3-methylphenyl)amino]-3-pyridinesulfonamide II is depicted in scheme 1 below.

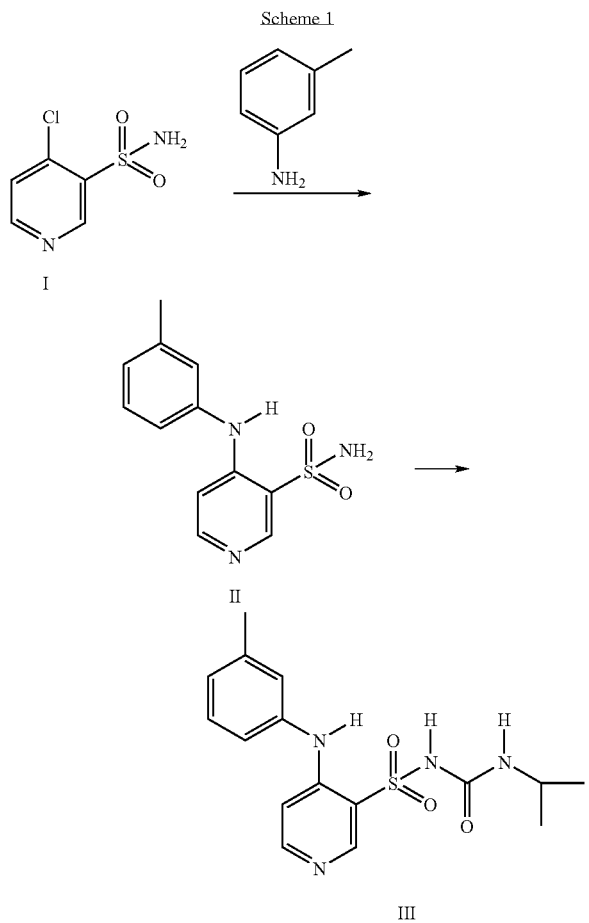

Scheme 1

U.S. RE 30,633 (1981, A. Christiaens Societe Anonyme, Belgium) disclose such a synthetic route to torsemide III and an intermediate II. For the preparation of II, the reaction is carried out in the presence of copper powder and at elevated temperature. The purification procedure of II is laborious as well in U.S. RE 30,633. Generally, it is disadvantageous to employ a heavy metal (such as copper) in the later stages of active pharmaceutical ingredient (API) production. Additional purification steps may be required to remove residual traces of the heavy metal from the API or its precursor.

U.S. RE 30,633 further provides for the preparation of torsemide III by the subsequent reaction of 4-[(3-methylphenyl)amino]-3-pyridinesulfonamide II with isopropyl isocyanate in the presence of triethylamine. The solvent system used in U.S. RE 30,633 is dichloromethane, dioxane or neat (i.e. no solvent added). After evaporative removal of the solvent, the mixture is clarified in aqueous sodium carbonate and further addition of acetic acid to furnish torsemide III.

Under such conditions the desired product, torsemide III is isolated in low yields with a high percentage of impurities, thus requiring additional purification steps.

U.S. Pat. No. 6,635,765 (Teva, 2001) discloses a process for preparing torsemide III comprising the step of reacting 3-sulfonamide-4-(3'-methylphenyl)aminopyridine II with isopropyl isocyanate in the presence of triethylamine in a solvent selected from the group consisting of acetonitrile, acetone, ethyl acetate, butyl acetate and mixtures thereof. Upon reaction completion, the pH is adjusted to 4.3 using aqueous hydrogen chloride solution and the precipitated product is isolated by filtration. It is then further purified by trituration in a mixture of acetonitrile and water. Thus, crude torsemide III is obtained with a purity of more than 98% and a chemical yield of 81.5%. In this process, once acidified, a large amount of water has to be added to precipitate the product III. However, many other organic impurities, including the toxic and difficult to remove N,N'-isopropyl urea (from the isopropyl isocyanate), precipitate out as well.

WO 03/097603 (Finetech Laboratories Ltd., 2003) discloses a process for manufacturing torsemide III. However, the process includes the use of isopropyl carbamate. This is not a commercially available compound and is prepared from the toxic and difficult to handle reagent, phenylchloroformate.

Furthermore, excessive exposure to carbamates has been shown to cause fatigue, joint and muscle pain and headaches. Additionally, laboratory experiments indicate that some carbamates have mutagenic or carcinogenic properties.

Furthermore, although WO 03/097603 describes a synthesis for the manufacture of the intermediate II where copper is absent, based on Example 11 the solvent used is methyl ethyl ketone and the reaction does not go to completion. The yield is 91.4% and the purity is only 99.0%, with 0.5% of the 4-chloro-3-pyridine sulfonamide starting material still present.

Once again, the torsemide III is isolated in low yields with an impurity level of toxic material that is difficult to remove.

In summary, some of the disadvantages of the prior art processes include:
i) the purity of the isolated torsemide is low thereby requiring additional steps to obtain pharmaceutically acceptable substance;
ii) the chemical yield of 81.5% for the crude torsemide is low;
iii) because water is introduced to isolate the torsemide during the acidification step, the torsemide is contaminated with N,N'-isopropyl urea;
iv) potential carcinogenic or mutagenic isocarbamate is used;

v) heavy metal usage requires removal thereof, which is difficult.

The yields of the prior art processes are low, highly variable and are unsuitable when transiting to commercial production.

It is therefore necessary to overcome the deficiencies of the prior art and to develop a cost-effective, robust and scalable process to manufacture both torsemide III and torsemide intermediate II. A further objective is to develop a process for making torsemide III meeting the high purity specifications required for an API.

Further and other objects of the invention will become apparent to a person skilled in the art when reading the following.

SUMMARY OF THE INVENTION

It has been unexpectedly and surprisingly found that the torsemide intermediate II can be prepared by a method that, relative to the processes of the prior art, is facile and straightforward. We have found unexpectedly that by heating 4-chloro-3-pyridinesulfonamide I and m-toluidine in n-butanol, in the absence of any copper catalyst, it is possible to generate torsemide intermediate II as its hydrochloride salt in a very high yield (>98%). Even more conveniently, the product can be easily filtered. The fact that this coupling can be accomplished in the absence of copper is highly desirable in that it avoids any possibility of contamination of torsemide intermediate II and, similarly, torsemide III with a heavy metal such as copper.

In another aspect of this invention, it has been surprisingly found that highly pure torsemide can be prepared in one-step and without the need for additional purification when an inorganic base such as an alkali carbonate or alkali bicarbonate is used in the reaction of 3-sulfonamide-4-(3'-methylphenyl)aminopyridine and isopropyl isocyanate. Examples include sodium carbonate, lithium carbonate or potassium carbonate. Moreover, we have found that when the above reaction goes to completion, it produces an alkali torsemide mixture that is essentially insoluble in solvents such as acetone or ethyl acetate. This insolubility allows, upon cooling, convenient isolation by filtration of the alkali torsemide mixture largely free of organic impurities (generally over 99.5% by HPLC), including N,N'-isopropyl urea. The torsemide is then easily obtained by acidification of the alkali torsemide mixture in a water-based media using a water-soluble acid, such as acetic acid. Fortunately, the isolated torsemide retains the high purity of the alkali torsemide precursor. One skilled in the art will recognize that this process can be used to prepare the various known forms of torsemide known in the prior art under the appropriate conditions.

In another aspect of the invention, it has been found that torsemide can be made in the absence of triethylamine. Triethylamine is a hazardous compound with known short-term and long-term health effects. Thus, avoidance of this compound is beneficial as well.

According to one aspect of the invention, there is provided a process for preparing torsemide or salts thereof comprising:
a) reacting II with isopropyl isocyanate in the presence of an alkali carbonate or bicarbonate and an organic solvent, preferably in the absence of triethylamine to form an alkali torsemide mixture,
b) recovering the alkali torsemide mixture, and
c) if desired, recovering the torsemide by acidification of the alkali torsemide mixture.

Preferably, the alkali carbonate is sodium carbonate, potassium carbonate, or lithium carbonate.

Preferably, the alkali bicarbonate is sodium bicarbonate, potassium bicarbonate, or lithium bicarbonate.

Preferably, the organic solvent is selected from the group consisting of acetone, ethyl acetate, acetonitrile, methyl isobutyl ketone and mixtures thereof.

Preferably, the alkali torsemide mixture is converted to torsemide by dissolving in water followed by acidification.

Preferably, the acid used for acidification is a water soluble acid, preferably acetic acid.

According to another aspect of the invention, there is provided a process for preparing II comprising reacting I with m-toluidine in an organic solvent to form II, wherein said process is carried out in the absence of at least one of the following:
i) a copper catalyst; and/or
ii) triethylamine.

Preferably, the organic solvent is a $C_1$-$C_6$ alcohol, preferably n-butanol.

DETAILED DESCRIPTION OF THE INVENTION

Example 1

Preparation of 4-[(3-methylphenyl)amino]-3-pyridinesulfonamide hydrochloride (II):

A 2-L, three-necked flask equipped with mechanical stirrer, thermometer and condenser was charged with 4-chloro-3-pyridinesulfonamide I (300.0 g, 1.56 mol), m-toluidine (200.3 g, 1.87 mol) and 1200 mL n-butanol. The reaction mixture was heated for 2-4 hours and then cooled to room temperature. The solid was filtered and washed with n-butanol. After drying, 4-[(3-methylphenyl)amino]-3-pyridinesulfonamide hydrochloride (457.1 g, 98%) was obtained as pale-yellow solid having a purity of 99.96% by HPLC.

Example 2

Preparation of N-[[(1-Methylethyl)amino]carbonyl]-4-[(3-methylphenyl)amino]-3-pyridinesulfonamide (Torsemide, III):

A 2-L, three-necked flask equipped with mechanical stirrer, thermometer and condenser was charged with 4-[(3-methylphenyl)amino]-3-pyridinesulfonamide II (100.0 g, 0.38 mol), sodium carbonate (40.3 g, 0.38 mol), isopropyl isocyanate (35.6 g, 0.42 mol) and acetone (1-L). The reaction mixture was heated at reflux until reaction completion (monitored by TLC or $^1$H-NMR, generally 8~20 h). The reaction mixture was cooled to room temperature and the solid was isolated by Buchner filtration. The filter cake was washed with 250 mL acetone to afford sodium torsemide mixture as a white solid. The filter cake was dissolved in 800 mL water and acetic acid (45.5 g, 0.76 mol) was added slowly. The resulting suspension was stirred for 2 h and the solid was filtered, washed with 250 mL water, and dried under vacuum at 50° C. for 12~16 h to yield 116.6 g torsemide as white solid (117.8 g, 89% yield, purity of 99.54% by HPLC).

Example 3

Preparation of N-[[(1-Methylethyl)amino]carbonyl]-4-[(3-methylphenyl)amino]-3-pyridinesulfonamide (Torsemide, III):

A 3-L, three-necked flask equipped with mechanical stirrer, thermometer and condenser was charged with 4-[(3-methylphenyl)amino]-3-pyridinesulfonamide II (100.0 g, 0.38 mol), potassium carbonate (52.4.3 g, 0.38 mol), isopropyl isocyanate (35.6 g, 0.42 mol) and acetone (1.8 L). The reaction mixture was heated at reflux until reaction completion (monitored by TLC or $^1$H-NMR, generally 8~20 h) whereupon it was cooled to room temperature and the solid was isolated by Buchner filtration. The filter cake was washed with 250 mL acetone to afford potassium torsemide mixture as white solid. The filter cake was dissolved in 800 mL water and acetic acid (45.5 g, 0.76 mol) was added slowly. The resulting suspension was stirred for 2 h and the solid was filtered, washed with 250 mL water, and dried under vacuum at 50 degree for 12~16 h to yield 116.6 g torsemide as white solid (116.3 g, 88% yield, purity of 99.61% by HPLC).

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A process for preparing torsemide or salts thereof comprising:
    a) reacting a compound of formula II

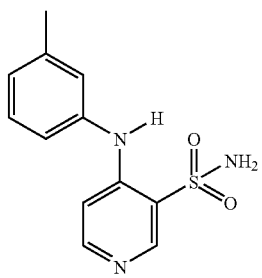

with isopropyl isocyanate in the presence of an alkali carbonate or bicarbonate and an organic solvent selected from the group consisting of ethyl acetate, acetonitrile, acetone, methyl isobutyl ketone and mixtures thereof to form an alkali torsemide mixture,
    b) recovering the alkali torsemide mixture as a salt,
    c) optionally recovering the torsemide by acidification of the alkali torsemide mixture;
    d) wherein step a) is carried out in the absence of triethylamine and water.

2. A process for preparing a compound of formula II

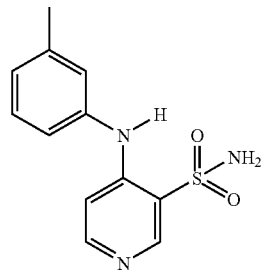

comprising reacting a compound of formula I

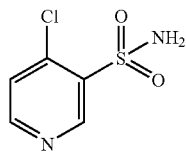

with m-toluidine in an organic solvent selected from the group consisting of a C1 to C6 alcohol to form a compound of formula II

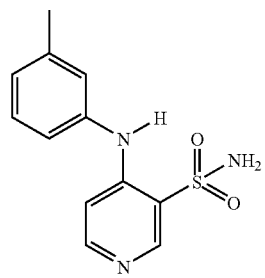

wherein said process is carried out in the absence of at least one of the following:
    i) a copper catalyst; and/or
    ii) triethylamine.

3. A process for preparing a compound of formula II

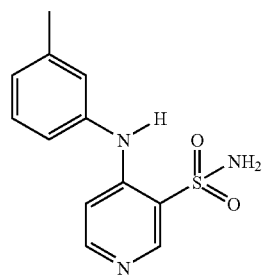

comprising reacting a compound of formula I

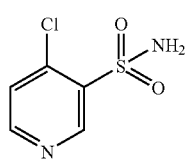

with m-toluidine in an organic solvent selected from the group consisting of n-butanol to form a compound of formula II

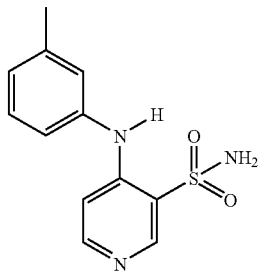

wherein said process is carried out in the absence of at least one of the following:
   i) a copper catalyst; and/or
   ii) triethylamine.

4. The process of claim 1 wherein the alkali carbonate is sodium carbonate, potassium carbonate, or lithium carbonate.

5. The process of claim 1 wherein the alkali bicarbonate is sodium bicarbonate, potassium bicarbonate, or lithium bicarbonate.

6. The process of claim 1 wherein the alkali torsemide mixture is converted to torsemide by dissolving in water followed by acidification.

7. The process of claim 1 wherein the acid used for acidification is a water soluble acid.

8. The process of claim 1 wherein the acid used for acidification is acetic acid.

9. The process of claim 1, 2 or 3 wherein the purity of the torsemide is at least about 99.5%.

10. The process of claim 1, 2 or 3 wherein the purity of torsemide is at least 98%.

* * * * *